United States Patent
Fago (10) Patent No.: US 8,986,251 B2
(45) Date of Patent: Mar. 24, 2015

(54) METHOD OF USING A SYRINGE PLUNGER ADAPTER

(75) Inventor: Frank M. Fago, Mason, OH (US)

(73) Assignee: Mallinckrodt LLC, Hazelwood, MO (US)

(*) Notice: Subject to any disclaimer, the term of this patent is extended or adjusted under 35 U.S.C. 154(b) by 1751 days.

(21) Appl. No.: 12/296,142

(22) PCT Filed: Nov. 13, 2007

(86) PCT No.: PCT/US2007/023967
§ 371 (c)(1),
(2), (4) Date: Oct. 6, 2008

(87) PCT Pub. No.: WO2008/063529
PCT Pub. Date: May 29, 2008

(65) Prior Publication Data
US 2009/0112087 A1   Apr. 30, 2009

Related U.S. Application Data

(60) Provisional application No. 60/860,601, filed on Nov. 22, 2006.

(51) Int. Cl.
*A61M 37/00*   (2006.01)
*A61M 31/00*   (2006.01)
(Continued)

(52) U.S. Cl.
CPC ....... *A61M 5/14546* (2013.01); *A61M 5/14566* (2013.01); *A61M 5/31515* (2013.01)
USPC ............................. 604/131; 604/500; 604/507

(58) Field of Classification Search
CPC ..................... A61M 5/14248; A61M 5/14244; A61M 5/172; A61M 5/1413; A61M 2005/206

USPC .................. 604/131, 181, 500, 503, 507, 514
See application file for complete search history.

(56) References Cited

U.S. PATENT DOCUMENTS

| 4,636,198 A | 1/1987 | Stade |
| 4,677,980 A | 7/1987 | Reilly et al. |

(Continued)

FOREIGN PATENT DOCUMENTS

| WO | WO 2004/000392 | 12/2003 |
| WO | WO 2006/091695 | 8/2006 |

OTHER PUBLICATIONS

Color photo of packaging for Ultraject™ prefilled syringe having 125 mL of Optiray™ 320 contrast media therein, Jul. 2005.

(Continued)

*Primary Examiner* — Kevin C Sirmons
*Assistant Examiner* — Pritesh Patel
(74) *Attorney, Agent, or Firm* — James L. Johnson; Marsh Fischmann & Breyfogle LLP (57) ABSTRACT

The invention relates to an adapter for a syringe plunger. The adapter of some embodiments may include a first side adapted to interface with a syringe plunger and an opposing a second side adapted to interface with a drive ram of a medical fluid injector. The adapter may include a peripheral side surface exhibiting a thickness and may include what may be characterized as at least one mating section adapted to engage with the syringe plunger. The mating section(s) may include a channel extending through the entire thickness of the adapter. In some embodiments, the mating section(s) may include a stop adjacent the channel that extends less than the entirety of the thickness of the adapter.

18 Claims, 8 Drawing Sheets

(51) Int. Cl.
*A61M 5/145* (2006.01)
*A61M 5/315* (2006.01)

(56) References Cited

U.S. PATENT DOCUMENTS

| | | | |
|---|---|---|---|
| 4,705,509 A | 11/1987 | Stade | |
| 5,104,386 A * | 4/1992 | Alzain | 604/232 |
| 5,383,858 A | 1/1995 | Reilly et al. | |
| 5,415,645 A * | 5/1995 | Friend et al. | 604/110 |
| 5,456,669 A * | 10/1995 | Neer et al. | 604/154 |
| 5,520,653 A | 5/1996 | Reilly et al. | |
| 5,865,805 A | 2/1999 | Ziemba | |
| 6,312,410 B1 | 11/2001 | Yamamoto | |
| 6,336,913 B1 | 1/2002 | Spohn et al. | |
| 6,533,758 B1 | 3/2003 | Staats et al. | |
| 6,676,634 B1 | 1/2004 | Spohn et al. | |
| 6,716,195 B2 | 4/2004 | Nolan, Jr. et al. | |
| 6,726,657 B1 | 4/2004 | Dedig et al. | |
| 6,743,205 B2 | 6/2004 | Nolan, Jr. et al. | |
| 6,764,466 B1 | 7/2004 | Staats et al. | |
| 6,821,013 B2 | 11/2004 | Reilly et al. | |
| 7,029,458 B2 | 4/2006 | Spohn et al. | |
| 7,033,338 B2 | 4/2006 | Vilks et al. | |
| 7,273,477 B2 | 9/2007 | Spohn et al. | |
| 7,553,293 B2 * | 6/2009 | Jensen et al. | 604/110 |
| 2003/0040719 A1 | 2/2003 | Spohn et al. | |
| 2003/0117888 A1 | 6/2003 | Reilly et al. | |
| 2004/0116893 A1 | 6/2004 | Spohn et al. | |

OTHER PUBLICATIONS

Color photo of packaging for Ultraject™ prefilled syringe having 100 mL of Optiray™ 320 contrast media therein, Jan. 2006.
Color photo of packaging for Ultraject™ prefilled syringe having 75 mL of Optiray™ 320 contrast media therein, Jan. 2006.
Color photo of packaging for Ultraject™ prefilled syringe having 50 mL of Optiray™ 320 contrast media therein, Jul. 2005.
Color photo of Ultraject™ prefilled syringe having 125 mL of Optiray™ 320 contrast media therein.
Color photo of Ultraject™ prefilled syringe having 100 mL of Optiray™ 320 contrast media therein.
Color photo of Ultraject™ prefilled syringe having 75 mL of Optiray™ 320 contrast media therein.
Color photo of Ultraject™ prefilled syringe having 50 mL of Optiray™ 320 contrast media therein.

* cited by examiner

METHOD OF USING A SYRINGE PLUNGER ADAPTER

CROSS REFERENCE TO RELATED APPLICATIONS

This patent application is a U.S. National Stage of and claims priority to International Application No. PCT/US2007/023967 filed 13 Nov. 2007, which claims priority to and is a non-provisional application of U.S. Provisional Application Ser. No. 60/860,601 filed 22 Nov. 2006, both of which are entitled "Universal Adapter for a Syringe Plunger." Priority is claimed to each patent application set forth in this Cross-Reference to Related Applications section.

FIELD OF THE INVENTION

The present invention relates generally to injectors and syringes for injecting medical fluids, and particularly to an adapter for a syringe plunger of a syringe.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

During many medical procedures, various fluids are injected into patients for purposes of diagnosis or treatment. An example of one such fluid is contrast media used to enhance diagnostic images generated in imaging procedures such as, for example, angiography, MRI and CT procedures. Injectors used in these procedures tend to be automated devices that expel the fluid from a syringe, through a tube, and into the subject. Often, the syringes will be purchased by the user prefilled with fluid, such as contrast media, in varying volumes.

Syringes used in the above-described imaging procedures generally include a barrel with a hollow interior and a discharge tip, and a syringe plunger disposed within the barrel. The rearward face of the syringe plunger of many of these syringes is formed by a backer plate. The backer plate generally includes a first portion that supports a rubber cap to form the forward facing surface of the syringe plunger, and a second portion forming a rearward facing surface including a coupling element, which is engageable with a plunger drive ram of the injector.

In many syringe plungers, the coupling element includes an extension or extensions referred to as a "bayonet coupling." A typical bayonet coupling may include two hook-like projections disposed opposite one another and protruding from the rearward facing surface of the backer plate. Each of the hook-like projections may include a stem portion, which projects from the rearward facing surface parallel to the longitudinal axis of the plunger, and a transverse arm portion, which extends from the proximal end of the stem portion in a direction perpendicular to the longitudinal axis of the plunger and toward the longitudinal axis of the plunger. When the syringe, including the syringe plunger and associated backer plate, is inserted into and coupled to an injector, the bayonet coupling contacts and couples to a plunger coupling element located on the forward end of the plunger drive ram. A typical plunger coupling element may include a "T"-shaped extension that projects from the forward end of the drive ram such that the stem of the "T" extends from the drive ram along the longitudinal axis of the drive ram, and the cap of the "T" is nearest to the rearward facing surface of the syringe plunger as the syringe is inserted into the injector. The syringe may be inserted in a manner such that the transverse arms of the hook-like projections do not confront or contact the cap of the "T," but rather are inserted past the cap of the "T." Once the transverse arms are positioned proximally of the top of the "T" of the T-shaped extension, the syringe may then be rotated relative to the plunger drive ram to bring the transverse arms of the hook-like projections into a confronting relationship with the T-shaped extension, thereby connecting the backer plate of the syringe plunger to the plunger drive ram, with the cap of the "T" positioned between the transverse arms and the rear face of the backer plate.

In another example of a syringe plunger, the coupling element may be an extension referred to as a "button," which may include a shaft portion protruding from the rearward facing surface of the backer plate, topped by a cap portion. When the syringe, including the syringe plunger and associated backer plate is inserted into an injector, the button typically contacts a plunger coupling element, such as engagement jaws, located on the forward end of the plunger drive ram. These jaws may then snap around the button of the backer plate, thereby connecting the backer plate of the syringe plunger to the plunger drive ram.

One drawback of present injectors and syringes is in the differing coupling elements on various syringe plungers, and plunger coupling elements on plunger drive rams. Different syringes (e.g., those made by different companies) include different coupling elements on backer plates, and different injectors (e.g., those made by different companies) include different extensions on plunger drive rams, such that a particular syringe will not necessarily engage plunger drive rams of every type of injector. This may tend to result in a reduction of options that consumers have for syringes and injectors.

SUMMARY

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of features and aspects that may not be set forth below.

In one aspect, the present invention is directed to an adapter that may be utilized to adapt a syringe plunger (e.g., backer plate thereof) so that the syringe may be adapted for use with a desired medical fluid injector. This adapter may include at least one mating section on a peripheral side surface of the adapter that is designed to engage a plunger coupling element of the syringe plunger. The adapter may include an extension and/or a depression on a rearward face thereof. The extension and/or depression of the adapter may exhibit any design/configuration to provide a complimentary configuration that enables use with the desired medical fluid injector. For example, the adapter may include an extension in the form of a "button" having a shaft portion extending from a rearward face of the adapter and topped by a cap portion.

In some embodiments, the adapter may include a first side (e.g., a forward face), a second side (e.g., a rearward face opposite the first side), and at least one peripheral side surface. The first side of the adapter may be adapted to confront a backer plate of a syringe plunger when the adapter is connected to the syringe plunger. The first side of the adapter may include a protrusion that can engage with a recess on the backer plate of the syringe plunger. The second side of the adapter may include a "button" extension protruding therefrom. This extension may include a shaft portion and a cap portion. The peripheral side surface(s) of the adapter may include the mating section(s) adapted to engage the syringe plunger in a manner such that the adapter and the syringe plunger are at least temporarily interconnected. For instance, the mating section(s) of the peripheral side surface(s) may engage one or more hook-like projections protruding from the rearward face of the backer plate of the syringe plunger. As such, the peripheral side surface(s) of the adapter may include a plurality (e.g., two) oppositely disposed mating sections adapted to engage the hook-like projection(s) on the rear face of a backer plate. In some embodiments, at least one of the mating sections of the adapter may include an alignment surface, an engagement arm, a confronting surface, and/or a stop. In some embodiments, at least one of the hook-like projections may include a stem portion, which projects from the rearward face of the backer plate parallel to a longitudinal axis of the plunger, and/or a transverse arm portion, which extends from a proximal end of the stem portion in a direction perpendicular to the longitudinal axis of the plunger and toward the longitudinal axis of the plunger.

In use, the adapter of one exemplary embodiment is positioned in a first position with the alignment surface aligned with a first side of the hook-like projection. In this first position, the adapter is not engaged with the syringe plunger. Further, in this first position, a leading edge of the engagement arm is positioned proximal to a second side of the hook-like projection. The adapter is then rotated relative to the backer plate such that the alignment surface moves away from the hook-like projection, and the engagement arm rides under the transverse arm of the hook-like projection. As rotation continues, the confronting surface is brought alongside the transverse arm of the hook-like projection, and rotation continues until the stop abuts the second side of the hook-like projection. When the adapter is in this second position, the engagement arm is underneath the transverse arm and in confronting relationship therewith, and the confronting surface confronts a side of the transverse arm, such that the adapter is engaged with the backer plate of the syringe plunger. Due to the "button" extension projecting from the second side of the adapter, the syringe may now be used with injectors having a "jaw-and-button" coupling arrangement between the plunger drive ram and syringe plunger.

In another aspect, the present invention is directed to an injection system that includes an adapter described herein. For example, one injection system in accordance with the principles of the present invention may include a syringe having a barrel, a syringe plunger adapted to be disposed within the barrel, and an adapter. The adapter may have a first side adapted to confront the syringe plunger, a second side opposite the first side, and at least one peripheral side surface including at least one mating section having an alignment surface, an engagement arm, a confronting surface, and a stop. The second side of the adapter may include an extension projecting therefrom. This extension may include a shaft portion and a cap portion.

Yet another aspect of the invention is directed to methods of connecting an adapter (such as those described herein) to and/or disconnecting an adapter from a syringe plunger. In one exemplary method, the adapter is positioned in a first position with the alignment surface aligned with a first side of the hook-like projection. In this first position, the adapter is not engaged with the syringe plunger, but a leading edge of an engagement arm of the adapter is positioned proximal to a side of a hook-like projection of the plunger backer plate. The adapter is then rotated relative to the backer plate such that an alignment surface thereof moves away from the hook-like projection, and such that an engagement arm of the adapter rides under a transverse arm of the hook-like projection. During this rotation, a confronting surface of the adapter may be brought alongside the transverse arm of the hook-like projection. This rotation may be continued until a stop of the adapter abuts the side of the hook-like projection. When the adapter is in this second position, the engagement arm may be underneath the transverse arm in confronting relationship therewith, and the confronting surface may confront a side of the transverse arm such that the adapter may be engaged with the backer plate of the syringe plunger. The syringe may now be used with injectors having a "jaw-and-button" coupling arrangement between the plunger drive ram and syringe plunger.

Various refinements exist of the features noted above in relation to the various aspects of the present invention. Further features may also be incorporated in these various aspects as well. These refinements and additional features may exist individually or in any combination. For instance, various features discussed below in relation to one or more of the illustrated embodiments may be incorporated into any of the above-described aspects of the present invention alone or in any combination. Again, the brief summary presented above is intended only to familiarize the reader with certain aspects and contexts of the present invention without limitation to the claimed subject matter.

DETAILED DESCRIPTION OF SPECIFIC EMBODIMENTS

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Figures 1, 2:
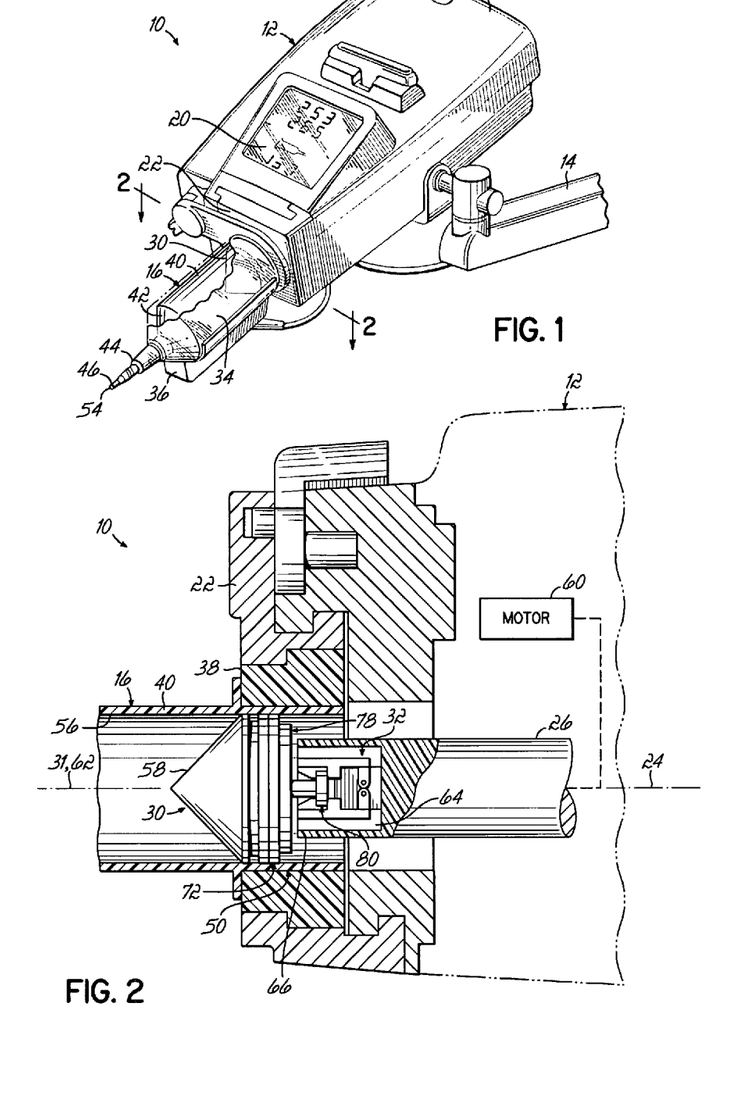
FIG. 1 is a perspective view of an injector head of an injector having a syringe attached thereto.
FIG. 2 is a cross-sectional view of the injector head and syringe of FIG. 1 taken along line 2-2.

Referring to FIG. 1, an injector 10 is depicted, having an injector head 12 attached to an arm 14, which in turn may be mounted to a support surface (e.g., ceiling, wall, floor joint (not shown)). This attachment of the injector head 12 to the arm 14 preferably allows motion of the injector head 12 in a manner such that it may be positioned in a desired orientation to receive and load a syringe 16 and to inject fluids into a subject (not shown). Surrounding the inner mechanism of the injector 10 is an injector housing 18. This housing 18 includes a display panel 20 that may be utilized, for example, to aid an operator of the injector 10 in monitoring amounts of fluid injected into a subject.

On a forward end of the injector housing 18, at least generally positioned between the injector 10 and the syringe 16, is a face plate 22. The face plate 22 may be mounted onto the injector housing 18 in any appropriate manner. For instance, the face plate 22 may be mounted onto the injector housing 18 by sliding the face plate 22 onto the injector housing 18 along a plane perpendicular to a longitudinal axis 24 of motion of a plunger drive ram 26 of the injector 10. One purpose of this face plate 22 may be to facilitate connection between the injector housing 18 and the syringe 16. Another purpose of the face plate 22 may be to facilitate disengagement of a coupling element 28 of a syringe plunger 30 from a coupling mechanism 32 of the plunger drive ram 26. For example, a syringe may be loaded into and coupled to the injector, such as at the face plate, by engaging respective mating sections on the outer surface of the syringe and on the face plate. In certain embodiments, disengagement of the syringe 16 from the face plate 22 may be affected by moving the face plate 22 transverse to the longitudinal axis 24 of the plunger drive ram 26. An at least generally similar transverse face plate motion has previously been used in rear or breech loading injectors (e.g., Angiomat 3000 and 6000, as well as CT 9000, all of which are/were manufactured by Liebel-Flarsheim Company). In addition to or as an alternative to transverse motion, face plates of some embodiments may be capable of pivotal motion (e.g., rotational motion about an axis) to enable rear loading a new syringe into a pressure jacket 34 of the injector 10. Likewise, the face's plate capability for pivotal motion may enable unloading or removing a used syringe from the pressure jacket 34, for example, after the face plate 22 has been laterally moved to disengage the rearwardly extending syringe plunger button and the drive ram jaws. Incidentally, while the injector 10 shown in FIG. 1 includes the face plate 22, it should be noted that principles of the invention also apply to injectors having other face plate designs as well as to injectors that do not employ face plates.

The pressure jacket 34 of the injector 10 may extend outwardly from the injector 10 (e.g., the face plate 22 thereof) any may be utilized to house the syringe 16 during an injection procedure. The syringe 16 and pressure jacket 34 are preferably constructed such that they collectively withstand injection pressures created by the injector 10 during an injection procedure. While the injector 10 is shown as having the pressure jacket 34, it should be noted that principles of the invention apply to injectors that include pressure jackets exhibiting other designs as well as to injectors that do not include a pressure jacket.

A cradle 36 is shown as being operatively connected to the injector 10. The cradle 36 may extends from the front surface 38 of the face plate 22 and/or may support the syringe 16 and pressure jacket 34. The cradle 36 may include a mechanism to warm the contents of the syringe 16. This warming feature, at least in some embodiments, allows the contents of a syringe 16 to be substantially maintained at a particular desired temperature or within a particular desired temperature range while the syringe 16 is attached to the injector 10. As such, it may be preferred for the syringe 16 of some embodiments to be held in proximity with the cradle 36 such that the media, or other fluid, within the syringe 16 may be warmed.

Figure 7:
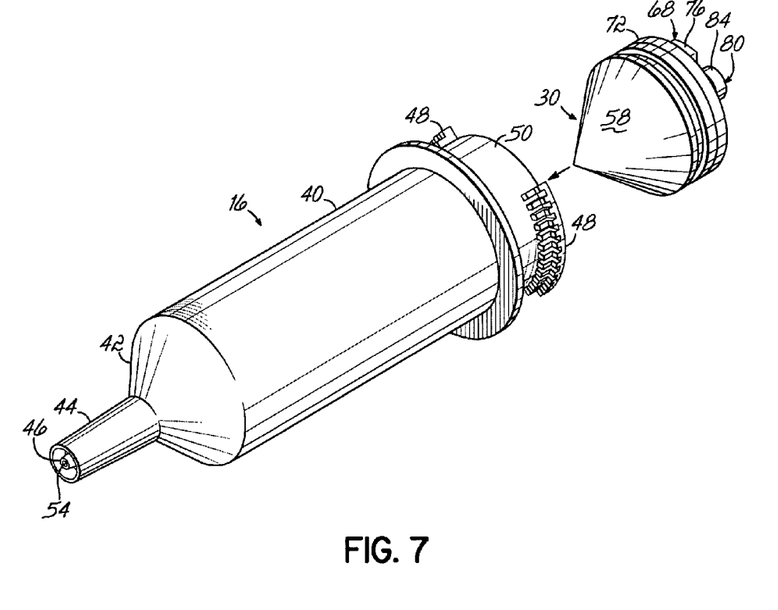
FIG. 7 is a perspective view showing insertion of a syringe plunger into a syringe body.
Figure 8:
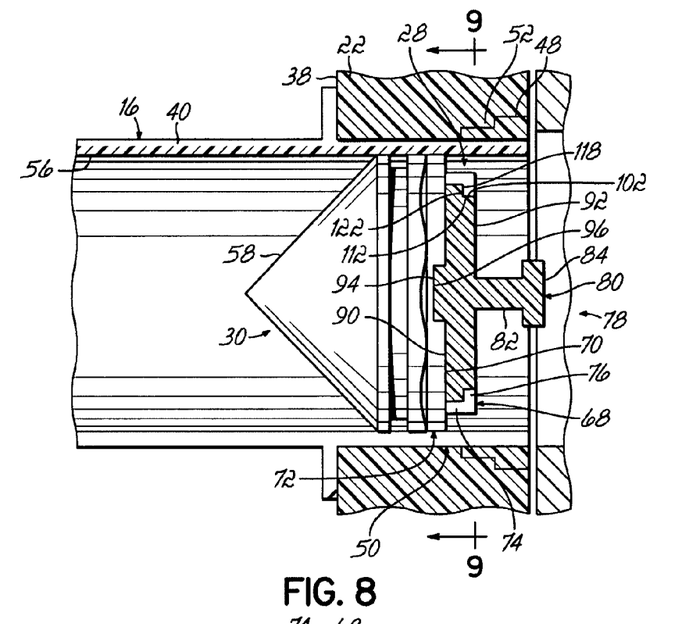
FIG. 8 is a cross-sectional view of a syringe plunger having an adapter in accordance with the principles of the present invention attached thereto and engaged with the plunger drive ram of an injector.
Figure 9:
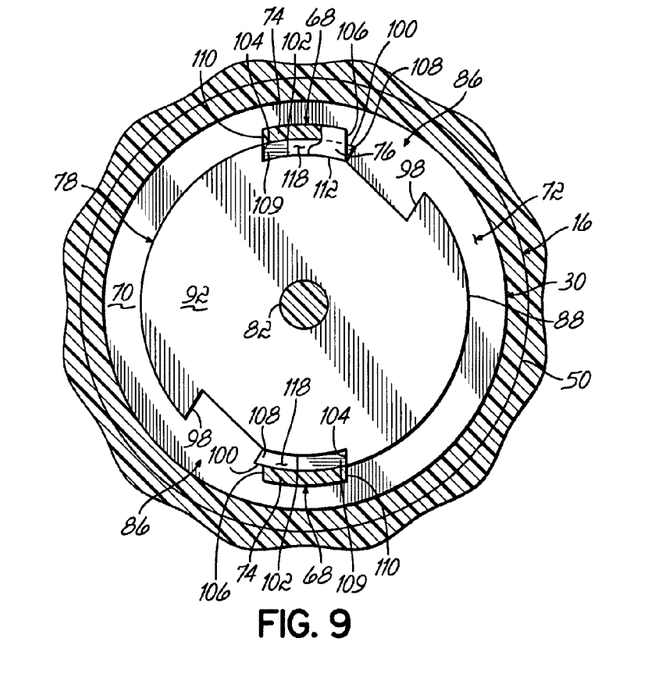
FIG. 9 is a cross-section of FIG. 8 taken along lines 9-9 of FIG. 8.

The syringe 16 includes a cylindrical barrel or body 40, which at its forward end is integral with a conical front wall section 42. A neck 44, terminating in discharge tip 46, extends forwardly from and is integral with the front wall section 42. The body of the syringe 16 snugly engages the interior walls of the pressure jacket 34. This syringe 16 includes a syringe mating section 48 (FIG. 7-8), which may be in the form of a radially outwardly extending annular flange, and which may be positioned in a plane perpendicular to the axis 24 of and integral with a rear end 50 of the body 40 of the syringe 16. The syringe mating section 48 is arranged, when the syringe 16 is located within the pressure jacket 34, to align with cooperating mating sections located on the rear end of the pressure jacket 34, or to cooperating mating sections 52 located in the face plate 22. In this manner, the syringe 16 and pressure jacket mating sections or face plate mating sections 52 facilitate the connection of the syringe 16 to the injector 10.

The neck 44 of the discharge tip 46 has an orifice 54 defined in its remote end, which communicates with an internal syringe cavity 56 formed within the neck 44, the front wall section 42, and the cylindrical barrel 40 of the syringe 16. A rear end of the cavity 56 is further defined by a forward facing conical surface 58 of the syringe plunger 30. The conical surface 58 is preferably of a slope, which substantially conforms to the slope of an interior of the front wall section 42. The syringe plunger 30 is preferably snugly slidable within the body 40 of the syringe 10 such that the cavity 56 is of a variable volume.

Figure 3:
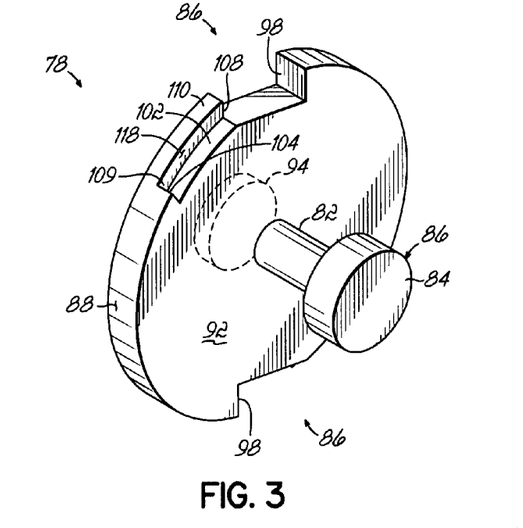
FIG. 3 is a perspective view of an adapter in accordance with the principles of the present invention.

Referring now to FIG. 2, the syringe plunger 30 can be seen more clearly within the cylindrical barrel 40 of the syringe 16. The syringe plunger 30 is attached to the plunger drive ram 26 of the injector 10. The plunger drive ram 26 is driven by a motor 60 to deploy the plunger drive ram 26 and syringe plunger 30 in a forward or rearward motion along an axis of symmetry 62 of the syringe cavity 56 to inject fluid into a subject or fill the syringe 16 with fluid, respectively. As illustrated in FIG. 2, the end of the drive ram 26 proximate to the syringe plunger 30 has a cavity 64 defined therein that is open at its front and in which is positioned the coupling mechanism 32. In another embodiment, the coupling mechanism 32 may be disposed on a forward end 66 of the drive ram 26. The syringe plunger 30 includes a plunger coupling element 28 on a rearward face 70 of the syringe plunger 30 (see FIG. 3).

Figure 4:
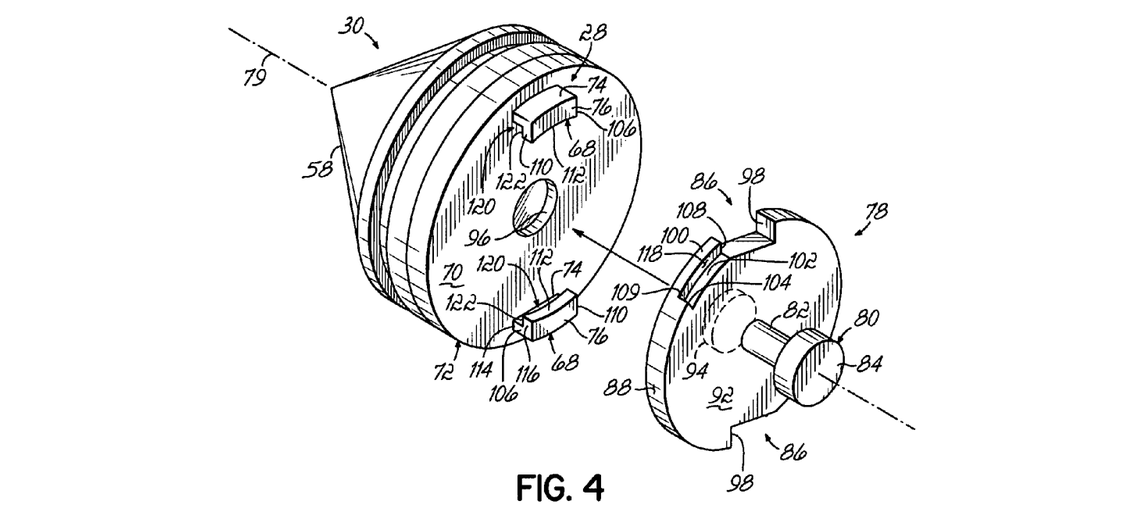
FIG. 4 is a perspective view of a syringe plunger and an adapter of the present invention, depicting a rearward face of the syringe plunger and a rearward face of the adapter.
Figure 5:
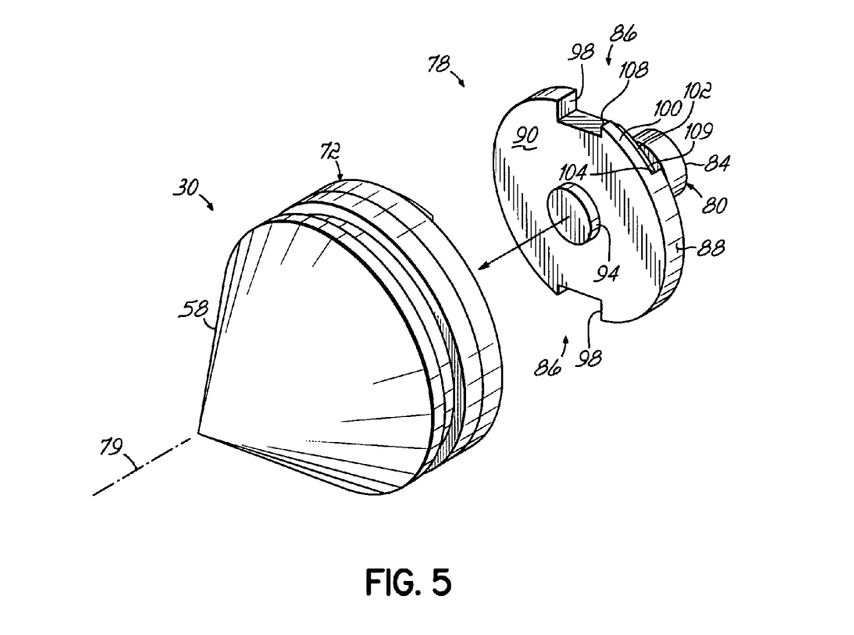
FIG. 5 is a perspective view of a syringe plunger and an adapter of the present invention, depicting a front surface of the adapter.

Referring now to FIG. 4, a plunger coupling element of the syringe plunger 30 is in the form of two hook-like projections 68 disposed opposite one another and protruding from the rearward face 70 of a backer plate 72 of the syringe plunger 30. Each of the hook-like projections 68 includes a stem portion 74, which projects from the rearward face 70 substantially parallel to a longitudinal axis 31 of the plunger 30, and a transverse arm portion 76, which extends from the proximal end of the stem portion 74 in a direction perpendicular to the longitudinal axis 31 of the plunger 30 and toward the longitudinal axis 31 of the plunger 30. When the syringe 16, including syringe plunger 30 and associated backer plate 72, is inserted into and coupled to an injector 10, the bayonet coupling would normally contact a plunger coupling element, such as a T-shaped extension (not shown), located on the forward end of the plunger drive ram. More specifically, the syringe is inserted into the injector 10 with the hook-like projections 68 disposed in a nonconfronting relationship with the T-shaped extension until the transverse arms 76 are positioned proximal of the top of the "T" of the T-shaped extension. The syringe 16 is then rotated relative to the plunger drive ram 26 to bring the transverse arms 76 of the hook-like projections 68 into a confronting relationship with the T-shaped extension (with the transverse arms 76 located proximal of the top of the "T"), thereby connecting the backer plate 72 of the syringe plunger 30 to the plunger drive ram 26.

The present invention is directed to syringe adapters that allows the syringe plungers having coupling mechanisms (e.g., hook-like coupling mechanisms) to be used with injectors having plunger coupling elements that do not include complementary coupling mechanisms (e.g., T-shaped extensions). For example, and referring to FIG. 3, the present invention provides an adapter 78 for a backer plate 72 of the plunger 30. This adapter 78 includes an extension 80 in the form of a "button" having a shaft portion 82 extending from a rearward face of the adapter 78, topped by a cap portion 84. The adapter 78 includes at least one mating section 86 on a peripheral side surface 88 thereof that is adapted to engage at least one hook-like projection 68 of a coupling element of a backer plate 72. Those skilled in the art will recognize that the description of a button on the rear face of the adapter 78 is merely exemplary, and any coupling element designed to mate with a plunger drive ram coupling mechanism may be present on the second side 92 of the adapter 78. Alternatively, there may be no coupling element present on the second side 92 of the adapter 78.

The coupling element of the adapter 78 and the coupling mechanism 32 of the plunger drive ram 26 are shown as being engaged in FIG. 2. As such, the syringe plunger 30 can be moved rearwardly via the attached adapter 86 being pulled rearward by the engaged plunger drive ram 26 under force of the injector motor 60 when it is desired to retract the syringe plunger 30, such as when filling the syringe 16. Alternatively, when using a syringe already having medical fluid disposed therein, the syringe plunger 30 can be moved forwardly via the attached adapter 86 being pushed forward by the engaged plunger drive ram 26 under force of the injector motor 60 when it is desired to expel fluid from the syringe 16, such as when injecting contrast media into a patient.

Referring now to FIGS. 3-9, the syringe plunger adapter 78 includes a first side 90 and an opposing second side 92, a peripheral side surface 88 exhibiting a first thickness of the adapter 78 between the first side 90 and second side 92, a channel 93 defined in the adapter 78 that extends an entirety of the first thickness through both the first and second sides 90, 92, and a stop 104 defined by the adapter 78 and extending from the second side 92 toward the first side 90, wherein the stop 104 is disposed adjacent the channel 93. The stop 104 has a thickness that is less than the entirety of the first thickness.

Further, the syringe plunger adapter 78 may be considered as having a reference axis 79 that extends through the first and second sides 90, 92. The peripheral side surface 88 is disposed about the reference axis 79, and the first thickness is measured parallel to the reference axis 79. A peripheral tier (a.k.a., an engagement arm) 100 may be located adjacent the peripheral side surface 88 and exhibits a second thickness less than the first thickness. The channel 93 is disposed at one end of the peripheral tier 100, and the stop 104 is disposed at another end of the peripheral tier 100 so that the peripheral tier 100 is located between the channel 93 and the stop 104. The stop 104 interconnects the peripheral tier 100 and the second side 92.

The first side 90 of the adapter 78 is designed to confront a backer plate 72 of a syringe plunger 30 when the adapter 78 is connected to the syringe plunger 30. A portion of that first side 90 may be defined by a protrusion 94 that can engage a recess 96 defined in the backer plate 72 of the syringe plunger 30. The second side 92 of the adapter 78 includes a "button" extension protruding therefrom. This extension 80 includes a shaft portion 82 and a cap portion 84. The peripheral side surface(s) 88 of the adapter 78 includes at least one mating section 86 adapted to engage a hook-like projection 68 protruding from the rearward face of the backer plate 72 of the syringe plunger 30. Particularly, the peripheral side surface 88 of the adapter 78 is shown as including two oppositely disposed mating sections 86 adapted to engage two oppositely disposed hook-like projections 68 on the rear face of the backer plate 72. Each mating section 86 includes an alignment surface 98, an engagement arm 100, a confronting surface 102, and a stop 104. The alignment surface 98 may be any surface that can confront a surface of a plunger coupling element 28 prior to movement, such as rotation of the adapter 78 relative to the plunger 30 to bring the two into full engagement. Thus, the alignment surface 98 allows the adapter 78 to be positioned relative to the syringe plunger 30 in a manner to facilitate engagement of those two components. The engagement arm 100 may be in the shape of a tier, or alternatively any other shape, that can interact with the plunger coupling element 28 in such manner as to prevent the adapter 78 from being moved in an axial direction relative to the syringe plunger 30 once the plunger 30 and adapter 78 are engaged. The confronting surface 102 may be any surface that can confront a surface of the plunger coupling element 28 to prevent movement of the adapter 78 in a direction perpendicular to the longitudinal axis 31 of the syringe plunger 30 once the plunger 30 and adapter 78 are engaged. And the stop 104 may be any surface that can confront a surface of the plunger coupling element 28 to stop movement, such as rotation, of the adapter 78 relative to the plunger 30 once the two are fully engaged. Each of the hook-like projections 68 includes a stem portion 74, which projects from the rearward face substantially parallel to the longitudinal axis 31 of the plunger 30, and a transverse arm portion 76, which extends from the proximal end of the stem portion 74 in a direction substantially perpendicular to the longitudinal axis 31 of the plunger 30 and toward the longitudinal axis 31 of the plunger 30.

Figure 6A:
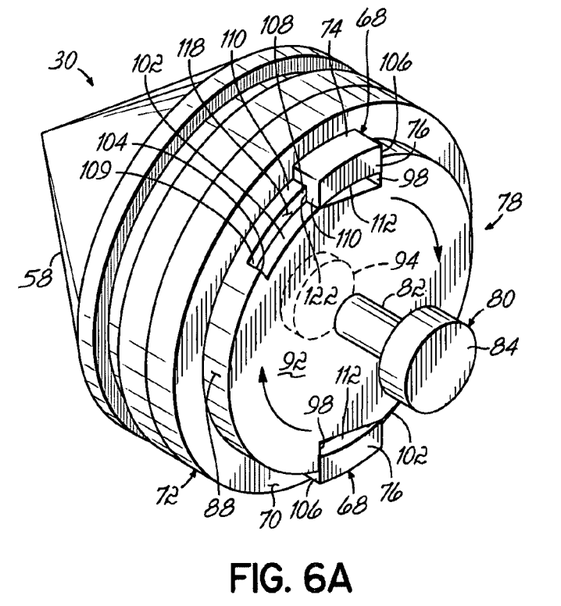
FIG. 6A is a perspective view of an adapter of the present invention in a first position aligned with, but not operatively coupled to, a syringe plunger.
Figure 6B:
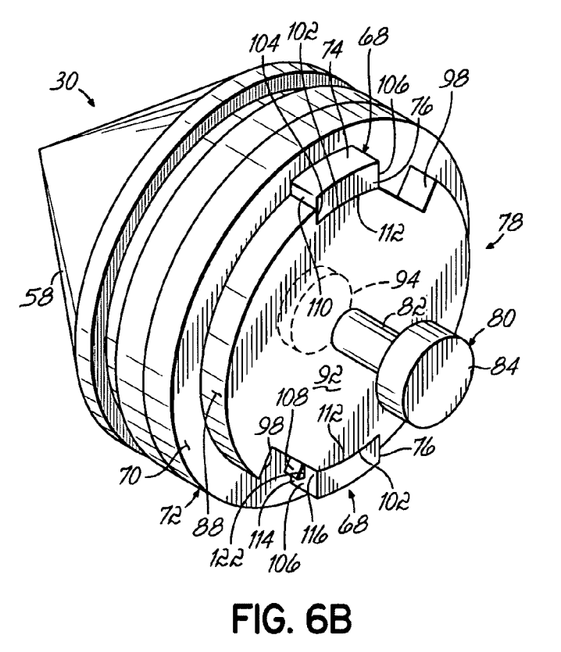
FIG. 6B is a perspective view of the adapter of FIG. 6A moved to a second position operatively coupled to the syringe plunger.

In use, the adapter 78 is originally positioned in a first position with the alignment surface 98 aligned with a first side 106 of the hook-like projection 68. In this first position, the adapter 78 is not engaged with the syringe plunger 30. Further, in this first position, a leading edge 108 of the engagement arm 100 is positioned proximal to a second side 110 of the hook-like projection 68. The adapter 78 is then rotated relative to the backer plate 72 such that the alignment surface 98 moves away from the hook-like projection 68, and the engagement arm 100 rides under the transverse arm 76 of the hook-like projection 68. As rotation continues, the confronting surface 102 is brought alongside the transverse arm 76 of the hook-like projection 68, and rotation continues until the stop 104 abuts the second side 110 of the hook-like projection 68. When the adapter 78 is in this second position, the engagement arm 100 is underneath the transverse arm 76 and in confronting relationship therewith, and the confronting surface 102 confronts a terminal end surface 112 of the transverse arm 76, such that the adapter 78 is engaged with the backer plate 72 of the syringe plunger 30. Due to the "button" extension projecting from the rearward face of the adapter 78, the syringe 16 may now be used with injectors having a "jaw-and-button" coupling arrangement between the plunger drive ram 26 and syringe plunger 30.

In one characterization, it may be said that the adapter 78 in accordance with the principles of the present invention is designed to be moved between at least a first position and a second position. In the first position, the adapter 78 is not engaged with the plunger coupling element 28 of the syringe plunger 30. In the second position, the adapter 78 is engaged with the plunger coupling element 28.

To accomplish this engagement, the plunger coupling element 28 includes at least one projection extending from the rear face 70 of the syringe plunger 30. This projection includes a stem portion 74 projecting from the rear face in a manner substantially parallel to the longitudinal axis 31 of the syringe plunger 30, and a transverse arm portion 76 extending from the stem portion 74 in a manner substantially perpendicular to the longitudinal axis 31. In other words, this projection is a hook-like projection 68, which, when no adapter 78 is present, would only be able to engage a plunger coupling element 28 of a drive ram exhibiting a complementary shape, such as a T-shaped extension. However, the mating section(s) 86 on the peripheral side surface(s) 88 of the adapter 78 allows the adapter 78 to engage the syringe plunger 30, thereby adapting the syringe 16 to be used with alternate injectors.

The mating of the adapter 78 to syringe plunger 30 may be facilitated due to the contour of the mating section(s) 86, which allow the adapter 78 to be brought into engagement with the syringe plunger 30 when the adapter 78 is moved from the first position to the second position. When initially in the first position, the alignment surface 98 is adapted to align with a first side of the plunger coupling element 28. More specifically, the adapter 78 is positioned such that the alignment surface 98 confronts, and possibly contacts, the first side 106 of the hook-like projection 68 of the plunger coupling element 28 in the illustrated embodiment. This first side 106 may comprise a side of the stem 74 of the hook-like projection 68, a side of the transverse arm 76 of the hook-like projection 68, or both. As the adapter 78 is moved to the second position, the alignment surface 98 will move away from (i.e., out of) confronting relationship with) the first side of the plunger coupling element 28. In the illustrated embodiment, the adapter 78 is moved from the first position to the second position by rotating the adapter 78 in a counter-clockwise direction. However, the movement of the adapter 78 is not so limited, and those skilled in the art will recognize that movement from the first to the second position may be accomplished by rotating in a clockwise direction, or by movement other than rotating the adapter 78.

As the adapter 78 is moved from the first to the second position, the engagement arm 100 is moved to engage the hook-like projection 68 of the plunger coupling element 28. More specifically, the engagement arm 100 includes a leading end 108, a trailing end 109, and an engagement surface 118 extending between the leading and trailing ends 108, 109. When the adapter 78 is in the first position, the leading end 108 is proximal to a second side of the plunger coupling element 28. In this configuration, the leading end 108 may contact the second side 110 of the hook-like projection 68 or may merely be adjacent the second side 110 of the hook-like projection 68.

During movement from the first to the second position, the engagement arm 100 moves into an engaging relationship with the hook-like projection 68 of the plunger coupling element 28, with the leading end 108 of the engagement arm 100 now positioned proximal to the first side 106 of the hook-like projection 68. As described above, the hook-like projection 68 of the plunger coupling element 28 includes a stem portion 74, which projects from the rearward face 70 parallel to the longitudinal axis of the plunger 30, and a transverse arm portion 76, which extends from the proximal end of the stem portion 74 in a direction perpendicular to the longitudinal axis of the plunger 30 and toward the longitudinal axis of the plunger 30. Thus, a "cavity" 120 is formed between the rear face 70 of the syringe plunger 30 and the transverse arm 76. When the adapter 78 is in the second position, the engagement arm 100 is disposed within this cavity 120, such that the engagement surface 118 confronts an inner side 122 of the transverse arm 76. In this second position then, the transverse arm 76 prevents the adapter 78 from being disengaged from the syringe plunger 30 by movement of the adapter 78 in a manner substantially parallel to the longitudinal axis 31 of the syringe plunger 30.

The trailing end 109 of the engagement arm 100 is adjacent to the stop 104. This stop 104 prevents the adapter 78 from continuing to be moved past the second position engagement of the adapter 78 and syringe plunger 30. Thus, the stop 104 is adapted to be remote from the plunger coupling element 28 when the adapter 78 is in the first position. However, as the adapter 78 is moved from the first position to the second position, the stop 104 is moved into confronting relationship, and possibly contacting relationship, with the second side 110 of the hook-like projection 68 of the plunger coupling element 28.

While the stop 104 aids in preventing the movement of the engagement arm 100 past the hook-like projection 68 (in a rotational direction in the illustrated embodiment), and the engagement arm 100 prevents the adapter 78 from disengaging the syringe plunger 30 by longitudinal movement, the confronting surface 102 of the adapter 78 aids in preventing disengagement of the adapter 78 due to movement of the adapter 78 transverse of the longitudinal axis 31 of the syringe plunger 30. In particular, the confronting surface 102 is adapted to be remote from the plunger coupling element 28 when the adapter 78 is in the first position. But when the adapter 78 is moved from the first position to the second position, the confronting surface 102 now confronts, and possibly contacts, the hook-like projection 68 of the plunger coupling element 28. In particular, when in the second position, the confronting surface 102 confronts a terminal end surface 112 of the transverse arm 76.

In another aspect, the present invention further includes a syringe assembly having an adapter 78 as described above. In particular, the syringe assembly includes a syringe barrel 40 and a plunger 30 disposable within the barrel 40, wherein a backside of the plunger 30 comprises at least one protrusion (e.g., an extension 80), and a plunger adapter 78 releasably interconnected with the plunger 30. The adapter 78 includes a first side 90 facing the backside of the plunger 30, a second side 92 opposing the first side, and a peripheral side surface 88 exhibiting a first thickness of the adapter 78 between the first side 90 and second side 92. The adapter 78 further includes a channel 93 defined in the adapter 78 that extends an entirety of the first thickness through both the first and second sides 90, 92 and a stop 104 defined by the adapter 78 and extending from the second side 92 toward the first side 90, but less than the entirety of the first thickness, wherein the stop 104 is disposed adjacent the channel 93. Further, the protrusion 80 of the plunger 30 is in contact with the stop 104 of the adapter 78.

Further, the adapter 78 in the syringe assembly has a reference axis 79 that extends through the first and second sides 90, 92. The peripheral side surface 88 is disposed about the reference axis 79, and the first thickness is measured parallel to the reference axis 79. A peripheral tier 100 may be located adjacent the peripheral side surface 88 and exhibiting a second thickness less than the first thickness, wherein at least a portion of the peripheral tier 100 is disposed between at least a portion of the protrusion 80 of the plunger 30 and at least a portion of the first side 90 of the adapter 78.

In another aspect, the present invention further includes an injection system having an adapter 78, as described above. Such an injection system more specifically includes a syringe 16 including a barrel 40, a syringe plunger 30 adapted to be disposed within the barrel 40, and an adapter 78 having a first side 90 adapted to be engaged with the syringe plunger 30, and a second side 92 including an extension 80 protruding therefrom, with at least one peripheral side surface 88 including at least one mating section 86 having an alignment surface 98, an engagement arm 100, a confronting surface 102, and a stop 104. The extension 80 includes a shaft portion 82 and a cap portion 84.

More specifically, the injector assembly includes a medical fluid injector 10 having a movable drive ram 26, a syringe 16 mounted to the injector 10, and a plunger adapter 78 releasably interconnected with the plunger 30. The syringe 16 comprises a syringe barrel 40 and a plunger 30 disposed within the barrel 40, wherein a backside of the plunger 30 comprises at least one protrusion 80. The adapter 78 comprises a first side 90 facing the backside of the plunger 30, a second side 92 facing the drive ram 26 of the injector 10, a peripheral side surface 88 exhibiting a first thickness of the adapter 78 between the first side 90 and second side 92, a channel 93 defined in the adapter 78 that extends an entirety of the first thickness through both the first and second sides 90, 92 a drive ram engaging feature associated with the first side 90 and in contact with the drive ram 26 of the injector 10, and a stop 104 extending out from the first side 90 and away from the second side 92, wherein the stop 104 is disposed adjacent the channel 93, and wherein the protrusion 80 of the plunger 30 is in contact with the stop 104 of the adapter 78.

Further, in the injector assembly, the drive ram engaging feature is associated with the second side 92 and in contact with the drive ram 26, and the peripheral tier 100 is located adjacent the peripheral side surface 88 and exhibits a second thickness less than the first thickness, wherein at least a portion of the peripheral tier 100 is disposed between at least a portion of the protrusion 80 of the plunger 30 and at least a portion of the first side 90 of the adapter 78.

Further still, in the injector assembly, a first projection 94 may extend out from the first side 90 of the adapter 78 and away from the second side 92 of the adapter 78, wherein the first projection 94 is disposed within the recess 96 defined in the backside of the plunger 30, and a drive ram engaging feature (e.g., extension 80) is associated with the second side 92 and in contact with the drive ram 26 of the injector 10.

In another aspect, the present invention also includes a method of operatively connecting an adapter 78 to, or removing an adapter 78 from, a syringe plunger 30. More specifically, the method comprises releasably interconnecting a plunger adapter 78 and a syringe plunger 30, wherein the releasably interconnecting plunger adapter 78 comprises contacting the syringe plunger 30 with the plunger adapter 78, and rotating at least one of the syringe plunger 30 and the plunger adapter 78 during the contacting, and contacting a drive ram engaging feature 80 of the plunger adapter 78 with a drive ram 26 of a medical fluid injector 10 once the plunger adapter 78 has been and remains releasably interconnected with the syringe plunger 30.

This method of operatively connecting an adapter 78 to a syringe plunger 30 may more particularly include the following steps. First, the adapter 78 is positioned in a first position with the alignment surface 98 aligned with a first side 106 of the hook-like projection 68. In this first position, the adapter 78 is not engaged with the syringe plunger 30, but a leading end 108 of the engagement arm 100 is positioned proximal to a second side 110 of the hook-like projection 68. The adapter 78 is then rotated relative to the backer plate 72 such that the alignment surface 98 moves away from the hook-like projection 68, and the engagement arm 100 rides under the transverse arm 76 of the hook-like projection 68. During this rotation, the confronting surface 102 is brought alongside the transverse arm 76 of the hook-like projection 68, and rotation continues until the stop 104 abuts the second side 110 of the hook-like projection 68. When the adapter 78 is in this second position, the engagement arm 100 is underneath the transverse arm 76 in confronting relationship with an inner side 122 thereof, and the confronting surface 102 confronts a side 116 of the transverse arm 76, such that the adapter 78 is engaged with the backer plate 72 of the syringe plunger 30. The syringe 16 may now be used with injectors having a "jaw-and-button" coupling arrangement between the plunger drive ram 26 and syringe plunger 30. Once the adapter/syringe combination is securely attached to injector head 12, the operator can begin the injection procedure. As the plunger drive ram 26 is advanced forward, the adapter 78 applies a motive force to the rear face 70 of syringe plunger 30, thus forcing fluid in the syringe 16 out of the neck 44 through the discharge tip 46 into the patient.

Once the injection procedure is completed, the operator can grasp the adapter/syringe combination and rotate the adapter 78 in the opposite direction from the locking direction (i.e., from the second position to the first position) to disengage the adapter 78 from the syringe 16. In this respect, the adapter 78 in accordance with the principles of the present invention is reusable.

Figure 10:
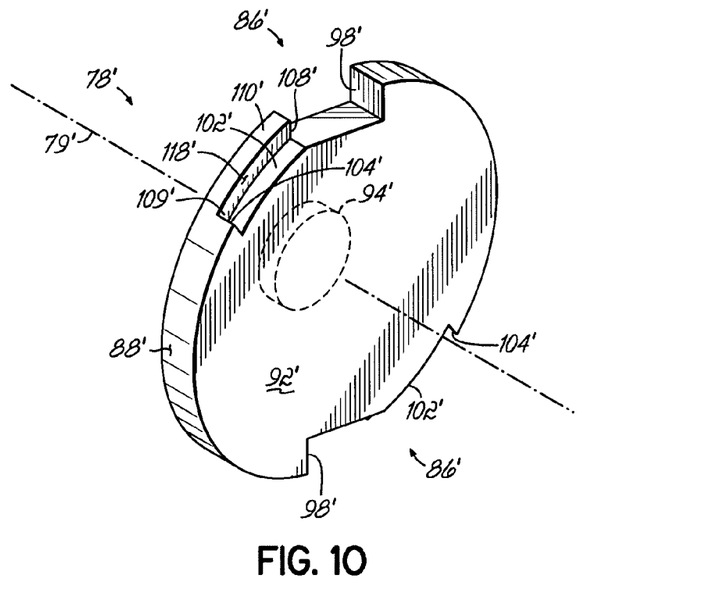
FIG. 10 is a perspective view of an alternate embodiment of an adapter in accordance with the principles of the present invention.
Figure 11A:
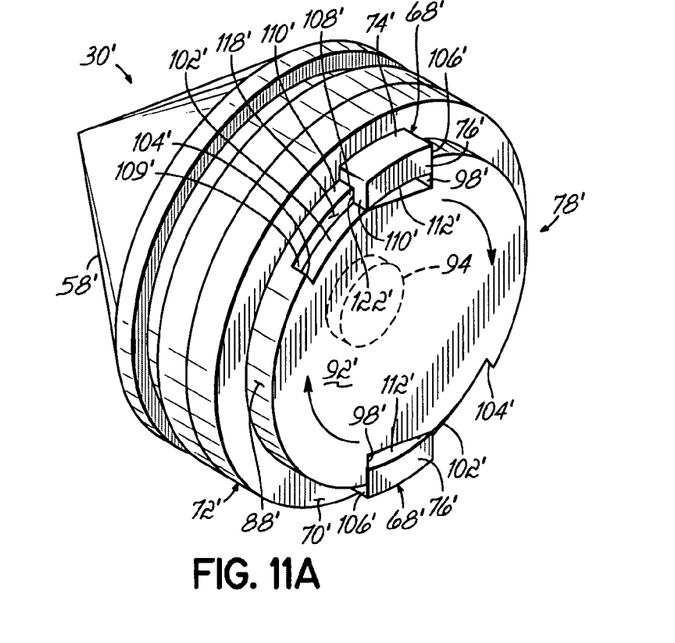
FIG. 11A is a perspective view of the adapter of FIG. 10 in a first position aligned with, but not operatively coupled to, a syringe plunger.
Figure 11B:
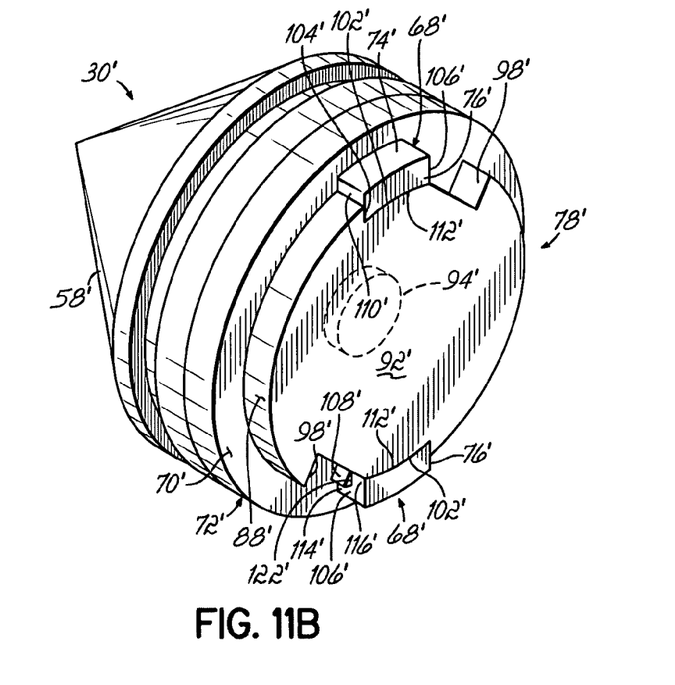
FIG. 11B is a perspective view of the adapter of FIG. 11A moved to a second position operatively coupled to the syringe plunger.
Figure 11C:
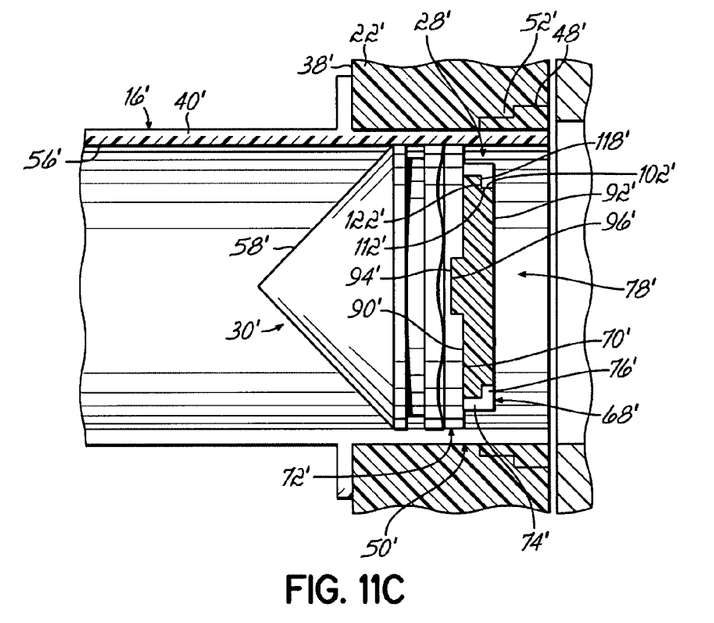
FIG. 11C is a cross-sectional view of a syringe having the adapter of FIG. 10 operatively coupled to a plunger thereof.

In a second embodiment of the adapter of the present invention, and referring to FIGS. 10 and 11, the adapter 78' includes a reference axis 79', a first side 90', a second side 92', and at least one peripheral side surface 88'. The first side 90' of the adapter 78' is adapted to confront a backer plate 72' of a syringe plunger 30' when the adapter 78' is connected to the syringe plunger 30'. A portion of that first side 90' may define a protrusion 94' that can engage a recess 96' on the backer plate 72' of the syringe plunger 30'. The second side 92' of the adapter 78' does not include any extension protruding therefrom. The at least one peripheral side surface 88' of the adapter 78' includes at least one mating section 86' adapted to engage a hook-like projection 68' protruding from the rearward face 70' of the backer plate 72' of the syringe plunger 30'. Particularly, the peripheral side surface 88' of the adapter 78' may include two oppositely disposed mating sections 86' adapted to engage two oppositely disposed hook-like projections 68' on the rear face 70' of a backer plate 72'. Each mating section 86' includes an alignment surface 98', an engagement arm 100', a confronting surface 102', and a stop 104'. Each of the hook-like projections 68' includes a stem portion 74', which projects from the rearward face 70' parallel to the longitudinal axis of the plunger 30', and a transverse arm portion 76', which extends from the proximal end of the stem portion 74' in a direction perpendicular to the longitudinal axis of the plunger 30' and toward the longitudinal axis of the plunger 30'.

In use, the adapter 78' is originally positioned in a first position with the alignment surface 98' aligned with a first side 106' of the hook-like projection 68'. In this first position, the adapter 78' is not engaged with the syringe plunger 30'. Further, in this first position, a leading edge 108' of the engagement arm 100' is positioned proximal to a second side 110' of the hook-like projection 68'. The adapter 78' is then rotated relative to the backer plate 72' such that the alignment surface 98' moves away from the hook-like projection 68', and the engagement arm 100' rides under the transverse arm 76' of the hook-like projection 68'. As rotation continues, the confronting surface 102' is brought alongside the transverse arm 76' of the hook-like projection 68', and rotation continues until the stop 104' abuts the second side 110' of the hook-like projection 68'. When the adapter 78' is in this second position, the engagement arm 100' is underneath the transverse arm 76' and in confronting relationship therewith, and the confronting surface 102' confronts a side 116' of the transverse arm 76', such that the adapter 78' is engaged with the backer plate 72' of the syringe plunger 30'. When using this adapter 78', the plunger drive ram 26 merely abuts the second side 92' of the adapter 78' to move it forward to expel fluid from the syringe 16. There is no positive engagement between the adapter 78' and plunger drive ram 26.

Figure 12A:
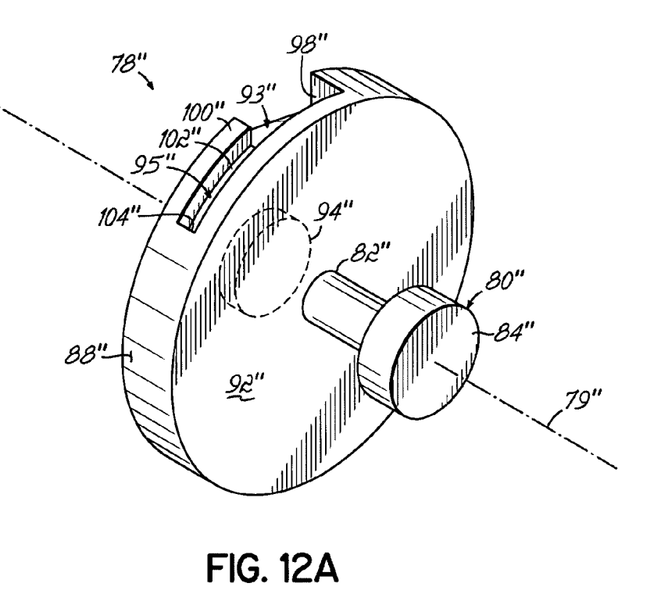
FIG. 12A is a perspective view of another alternate embodiment of an adapter in accordance with the principles of the present invention depicting a rearward face of the adapter.
Figure 12B:
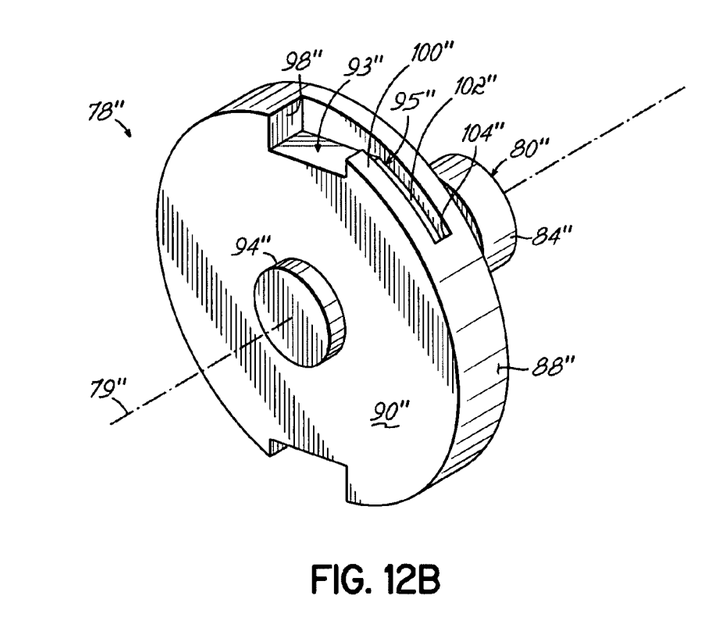
FIG. 12B is a perspective view of the adapter of FIG. 12A depicting a front surface of the adapter.

In a third embodiment, and referring now to FIGS. 12A-12B, the adapter 78" includes a first side 90" and an opposing second side 92", a peripheral side surface 88" exhibiting a first thickness of the adapter 78" between the first side 90" and second side 92", a channel 93" defined in the adapter 78" that extends within the first thickness from the first side 90" and terminating prior to the second side 92", and a stop 104" defined by the adapter 78".

Further, the syringe plunger adapter 78" may be considered as having a reference axis 79" that extends through the first and second sides 90", 92". The peripheral side surface 88" is disposed about the reference axis 79", and the first thickness is measured parallel to the reference axis 79". A peripheral tier (a.k.a., an engagement arm) 100" may be located adjacent the peripheral side surface 88" and exhibits a second thickness less than the first thickness. The channel 93" is disposed at one end of the peripheral tier 100", and the stop 104" is disposed adjacent to another end of the peripheral tier 100" so that the peripheral tier 100" is located between the channel 93" and the stop 104". The stop 104" extends within the first thickness between the first and second sides 90", 92". A cavity 95 is thus defined between the stop 104" and the channel 93".

The first side 90" of the adapter 78" is designed to confront a backer plate 72 of a syringe plunger 30 when the adapter 78" is connected to the syringe plunger 30. While a syringe plunger 30 (having a backer plate 72 with projection 68) is not shown in FIGS. 12A and 12B, the interaction of adapter 78" with same is similar to that described above with respect to the first and second embodiments of the adapter 78, 78'. Thus, the components discussed below can be seen with respect to those embodiments (as in FIGS. 6A, 6B, 11A, and 11B, for example). Thus, a portion of the first side 90" may be defined by a protrusion 94" that can engage a recess 96 defined in the backer plate 72 of the syringe plunger 30. The second side 92" of the adapter 78" includes a "button" extension protruding therefrom. This extension 80" includes a shaft portion 82" and a cap portion 84". The peripheral side surface(s) 88" of the adapter 78" includes at least one mating section 86" adapted to engage a hook-like projection 68" protruding from the rearward face of the backer plate 72 of the syringe plunger 30. Particularly, the peripheral side surface 88" of the adapter 78" is shown as including two oppositely disposed mating sections 86" adapted to engage two oppositely disposed hook-like projections 68 on the rear face of the backer plate 72. Each mating section 86" may include an alignment surface 98", an engagement arm 100", a confronting surface 102", and a stop 104". The alignment surface 98" may be any surface that can confront a surface of a plunger coupling element 28 prior to movement, such as rotation of the adapter 78" relative to the plunger 30 to bring the two into full engagement. Thus, the alignment surface 98" allows the adapter 78" to be positioned relative to the syringe plunger 30 in a manner to facilitate engagement of those two components. The engagement arm 100" may be in the shape of a tier (like the peripheral tier 100"), or alternatively any other shape, that can interact with the plunger coupling element 28 in such manner as to prevent the adapter 78" from being moved in an axial direction relative to the syringe plunger 30 once the plunger 30 and adapter 78" are engaged. The confronting surface 102" may be any surface that can confront a surface of the plunger coupling element 28 to prevent movement of the adapter 78" in a direction perpendicular to the longitudinal axis 31 of the syringe plunger 30 once the plunger 30 and adapter 78" are engaged. And the stop 104" may be any surface that can confront a surface of the plunger coupling element 28 to stop movement, such as rotation, of the adapter 78" relative to the plunger 30 once the two are fully engaged. Each of the hook-like projections 68 includes a stem portion 74, which projects from the rearward face substantially parallel to the longitudinal axis 31 of the plunger 30, and a transverse arm portion 76, which extends from the proximal end of the stem portion 74 in a direction substantially perpendicular to the longitudinal axis 31 of the plunger 30 and toward the longitudinal axis 31 of the plunger 30.

In use, the adapter 78" is originally positioned in a first position with the alignment surface 98" aligned with a first side 106 of the hook-like projection 68. In this first position, the adapter 78" is not engaged with the syringe plunger 30. Further, in this first position, a leading edge 108" of the engagement arm 100" is positioned proximal to a second side 110 of the hook-like projection 68. The adapter 78" is then rotated relative to the backer plate 72 such that the alignment surface 98" moves away from the hook-like projection 68, and the engagement arm 100" rides under the transverse arm 76 of the hook-like projection 68. The transverse arm 76 is thus moved into the cavity 95 of the adapter 78". As rotation continues, the confronting surface 102" is brought alongside the transverse arm 76 of the hook-like projection 68, and rotation continues until the stop 104" abuts the second side 110 of the hook-like projection 68. When the adapter 78" is in this second position, the engagement arm 100" is underneath the transverse arm 76 and in confronting relationship therewith, the confronting surface 102" confronts a terminal end surface 112 of the transverse arm 76, and the transverse arm 76 is disposed within the cavity 95, such that the adapter 78" is engaged with the backer plate 72 of the syringe plunger 30. Due to the "button" extension projecting from the rearward face of the adapter 78", the syringe 16 may now be used with injectors having a "jaw-and-button" coupling arrangement between the plunger drive ram 26 and syringe plunger 30.

Additional advantages and modifications will readily appear to those skilled in the art. The invention in its broader aspects is therefore not limited to the specific details, representative apparatus and methods, and illustrative examples shown and described. Accordingly, departures may be made from such details without departing from the scope or spirit of the general inventive concepts.

What is claimed is:

1. A method of operation for a medical fluid injector, the method comprising:
adapting a syringe plunger of a syringe so that the syringe may be utilized with a medical fluid injector, wherein the adapting comprises releasably interconnecting a plunger adapter and the syringe plunger, wherein the syringe plunger is disposed within a body of the syringe; wherein the syringe plunger comprises a backer plate; wherein the backer plate comprises a plurality of coupling mechanisms that are spaced from one another about a first longitudinal axis of the syringe plunger and that are disposed at a common location along this first longitudinal axis;
wherein the plunger adapter comprises a plurality of mating sections that are spaced from one another about a second longitudinal axis of the plunger adapter and that are disposed at a common location along this second longitudinal axis; and
wherein the releasably interconnecting comprises:
disposing the syringe plunger in a position where the backer plate of the syringe plunger projects toward the plunger adapter; and
rotating at least one of the syringe plunger and the plunger adapter relative to the other of the syringe plunger and plunger adapter after the disposing, wherein the rotating comprises causing each mating section of the plunger adapter to move into an engaged position with a corresponding coupling mechanism of the syringe plunger to connect the plunger adapter with the syringe plunger;
installing the syringe on the medical fluid injector after completion of the adapting;
contacting a drive ram engaging feature of the plunger adapter with a drive ram coupling mechanism of the medical fluid injector after the installing; and
moving the syringe plunger rearwardly while the plunger adapter and the syringe plunger remain releasably interconnected with one another, wherein the moving comprises pulling the plunger adapter rearward using a drive ram of the medical fluid injector and while the drive ram coupling mechanism remains in contact with the drive ram engaging feature of the plunger adapter.

2. The method of claim 1, wherein the disposing comprises aligning an alignment surface of a peripheral side surface of the plunger adapter with a protrusion on the backer plate of the syringe plunger, and wherein the rotating comprises distancing the alignment surface from the protrusion.

3. The method of claim 1, further comprising moving a peripheral tier of a peripheral side surface of the plunger adapter from a first position not engaged with a protrusion on the backer plate of the syringe plunger to a second position engaged with the protrusion during the rotating.

4. The method of claim 1, wherein the rotating comprises converging a stop on a peripheral side surface of the plunger adapter and a protrusion on the backer plate of the syringe plunger.

5. The method of claim 1, wherein the contacting a drive ram engaging feature is accomplished, at least in part, by moving at least one of the plunger adapter and the drive ram along a longitudinal axis of the drive ram.

6. The method of claim 1, wherein the moving comprises filling a syringe with medical fluid for use in a medical imaging procedure.

7. The method of claim 1, wherein the medical fluid comprises contrast media.

8. The method of claim 1, further comprising moving the syringe plunger forward while the plunger adapter and the syringe plunger remain releasably interconnected with one another, wherein moving the syringe plunger forward comprises pushing the plunger adapter forward using the drive ram of the medical fluid injector while the drive ram coupling mechanism remains in contact with the drive ram engaging feature of the plunger adapter.

9. The method of claim 8, wherein moving the syringe plunger forward comprises expelling medical fluid for use in a medical imaging procedure from the syringe.

10. The method of claim 9, wherein the medical fluid comprises contrast media.

11. A method of operation for a medical fluid injector, the method comprising:
adapting a syringe plunger for a syringe, the syringe plunger having a plurality of coupling mechanisms to be used with a medical fluid injector having a drive ram that does not include complimentary coupling mechanisms, wherein the adapting comprises releasably interconnecting a plunger adapter and the syringe plunger, wherein the syringe plunger is disposed within a barrel of the syringe;
wherein the syringe plunger comprises a backer plate; wherein the backer plate comprises the plurality of coupling mechanisms and that are spaced from one another about a first longitudinal axis of the syringe plunger and that are disposed at a common location along this first longitudinal axis;
wherein the plunger adapter comprises a plurality of mating sections that are spaced from one another about a second longitudinal axis of the plunger adapter and that are disposed at a common location along this second longitudinal axis; and
wherein the releasably interconnecting comprises:
disposing the syringe plunger in a position where the backer plate of the syringe plunger projects toward the plunger adapter; and
rotating at least one of the syringe plunger and the plunger adapter relative to the other of the syringe plunger and plunger adapter after the disposing, wherein the rotating comprises causing each mating section of the plunger adapter to move into an engaged position with a corresponding coupling mechanism of the syringe plunger to connect the plunger adapter with the syringe plunger;
installing the syringe on the medical fluid injector after completion of the adapting; and contacting a drive ram engaging feature of the plunger adapter with a drive ram coupling mechanism for a movable drive ram of a medical fluid injector after the installing.

12. The method of claim 11, wherein the contacting a drive ram engaging feature is accomplished, at least in part, by moving at least one of the plunger adapter and the drive ram along a longitudinal axis of the drive ram.

13. The method of claim 11, further comprising moving the syringe plunger within and relative to the barrel of the syringe while the plunger adapter and the syringe plunger remain releasably interconnected with one another.

14. The method of claim 13, wherein the moving comprises moving the syringe plunger rearwardly while the plunger adapter and the syringe plunger remain releasably interconnected with one another to draw medical fluid for use in a medical imaging procedure into the syringe.

15. The method of claim 14, wherein the medical fluid comprises contrast media.

16. The method of claim 13, wherein the moving comprises moving the syringe plunger forward while the plunger adapter and the syringe plunger remain releasably interconnected with one another.

17. The method of claim 16, wherein moving the syringe plunger forward comprises expelling medical fluid for use in a medical imaging procedure from the syringe.

18. The method of claim 17, wherein the medical fluid comprises contrast media.

\* \* \* \* \*